(12) United States Patent
Kjalke (10) Patent No.: US 7,015,194 B2
(45) Date of Patent: Mar. 21, 2006

(54) PHARMACEUTICAL COMPOSITION COMPRISING FACTOR VIIA AND ANTI-TFPI

(75) Inventor: Marianne Kjalke, Copenhagen N (DK)

(73) Assignee: Novo Nordisk A/S, Bagsvaerd (DK)

(*) Notice: Subject to any disclaimer, the term of this patent is extended or adjusted under 35 U.S.C. 154(b) by 272 days.

(21) Appl. No.: 10/271,926

(22) Filed: Oct. 16, 2002

(65) Prior Publication Data

US 2003/0073638 A1  Apr. 17, 2003

Related U.S. Application Data

(63) Continuation of application No. PCT/DK01/00324, filed on May 10, 2001.

(60) Provisional application No. 60/212,857, filed on Jun. 20, 2000, provisional application No. 60/206,212, filed on May 22, 2000, provisional application No. 60/206,194, filed on May 22, 2000.

(30) Foreign Application Priority Data

| May 10, 2000 | (DK) | ................................ 2000 00771 |
| May 10, 2000 | (DK) | ................................ 2000 00778 |
| Jun. 6, 2000 | (DK) | ................................ 2000 00871 |

(51) Int. Cl.
*A61K 38/36* (2006.01)
*C07K 14/745* (2006.01)

(52) U.S. Cl. .................... 514/2; 514/455; 530/380; 530/384; 549/392; 424/141.1; 424/145.1

(58) Field of Classification Search ............ 514/2, 514/455; 530/380, 384; 549/392; 424/141.1, 424/145.1
See application file for complete search history.

(56) References Cited

U.S. PATENT DOCUMENTS

| 4,382,083 | A | * | 5/1983 | Thomas ................... 424/94.64 |
| 5,622,988 | A |   | 4/1997 | Worsaae et al. ............ 514/455 |
| 6,310,183 | B1 | * | 10/2001 | Johannessen et al. ....... 530/384 |
| 2003/0040480 | A1 |   | 2/2003 | Rojkjaer |
| 2003/0054018 | A1 |   | 3/2003 | Hedner |
| 2003/0092627 | A1 |   | 5/2003 | Rojkjaer |
| 2003/0109446 | A1 |   | 6/2003 | Rojkjaer |
| 2003/0118574 | A1 |   | 6/2003 | Rojkjaer |
| 2003/0118580 | A1 |   | 6/2003 | Rojkjaer |
| 2003/0118582 | A1 |   | 6/2003 | Rojkjaer |
| 2003/0119723 | A1 |   | 6/2003 | Rojkjaer |
| 2003/0119741 | A1 |   | 6/2003 | Rojkjaer |
| 2003/0119743 | A1 |   | 6/2003 | Rojkjaer |
| 2003/0124118 | A1 |   | 7/2003 | Rojkjaer |
| 2003/0125256 | A1 |   | 7/2003 | Rojkjaer |
| 2003/0199444 | A1 |   | 10/2003 | Rojkjaer |
| 2003/0203845 | A1 |   | 10/2003 | Rojkjaer |
| 2004/0006020 | A1 |   | 1/2004 | Rojkjaer |
| 2004/0006021 | A1 |   | 1/2004 | Rojkjaer |
| 2004/0258690 | A1 |   | 12/2004 | Rojkjaer |

FOREIGN PATENT DOCUMENTS

| EP | 0082182 B1 | 7/1987 |
| EP | 0225160 B1 | 8/1991 |
| EP | 0558529 B1 | 1/1996 |
| WO | WO 92/07584 | 5/1992 |
| WO | WO 93/06855 | 4/1993 |
| WO | WO 94/02172 | 3/1994 |
| WO | WO 96/28153 | 9/1996 |
| WO | WO 98/58661 | 12/1998 |

OTHER PUBLICATIONS

Erhardsten et al. "Blocking of Tissue Factor Pathway Inhibitor (TFPI) Shortens the Bleeding Time in Rabbits With Antibody Induced Haemophilia A" Blood Coagulation and Fibrinolysis. No. 6, pp. 388-394. 1995.*
Baiai et al., J. Clin. Invest., vol. 79, pp. 1874-1878 (1987).
Broze et al., Biochemistry, vol. 29, No. 33, pp. 7539-7546 (1990).
Rapaport et al., Blood. vol. 73, No. 2, pp. 359-365 (1989).
Sandset et al., Thrombosis Research, vol. 47, pp. 389-401 (1987).

* cited by examiner

*Primary Examiner*—Anish Gupta
(74) *Attorney, Agent, or Firm*—Len S. Smith; Reza Green; Richard Bork (57) ABSTRACT

The present invention relates to the use of factor VIIa and TFPI inhibitor in the treatment or prophylaxis of bleeding episodes or coagulative treatment.

13 Claims, 5 Drawing Sheets

Figure 4: FVIIa, increasing concentrations.

Figure 5: FVIIa (10 nM) + increasing aTFPI concentrations

PHARMACEUTICAL COMPOSITION COMPRISING FACTOR VIIA AND ANTI-TFPI

CROSS REFERENCE TO RELATED APPLICATIONS

This application is a continuation of PCT/DK01/00324 filed on May 10, 2001, and claims priority under 35 U.S.C. 119 of Danish application no. PA 2000 00778 filed on May 10, 2000, Danish application no. PA 2000 00771 filed on May 10, 2000, Danish application no. PA 2000 00871 filed on Jun. 6, 2000, U.S. provisional application No. 60/206,194 filed on May 22, 2000, U.S. provisional application No. 60/206,212 filed on May 22, 2000, and U.S. provisional application No. 60/212,857 filed on Jun. 20, 2000, the contents of which are fully incorporated herein by reference.

FIELD OF THIS INVENTION

The present invention relates to a pharmaceutical composition comprising a Factor VIIa and a TFPI inhibitor. The invention also relates to the use of a combination of factor VIIa with TFPI inhibitor for the manufacture of a medicament for treatment of subjects suffering from bleeding episodes, or prevention hereof. The invention also relates to a method for treatment of bleeding episodes in subjects and to a method for enhancing clot formation in a subject. The present invention also relates to kits comprising these compounds.

BACKGROUND OF THE INVENTION

Haemostasis is initiated by the formation of a complex between tissue factor (TF) being exposed to the circulating blood following an injury to the vessel wall, and FVIIa which is present in the circulation in an amount corresponding to about 1% of the total FVII protein mass. This complex is anchored to the TF-bearing cell and activates FX into FXa and FIX into FIXa on the cell surface. FXa activates prothrombin to thrombin, which activates FVIII, FV, FXI and FXIII. Furthermore, the limited amount of thrombin formed in this initial step of haemostasis also activates the platelets. Following the action of thrombin on the platelets these change shape and expose charged phospholipids on their surface. This activated platelet surface forms the template for the further FX activation and the full thrombin generation. The further FX activation on the activated platelet surface occurs via a FIXa–FVIIIa complex formed on the surface of the activated platelet, and FXa then converts prothrombin into thrombin while still on the surface. Thrombin then converts fibrinogen into fibrin which is insoluble and which stabilises the initial platelet plug. This process is localized to the site of TF exposure thereby minimizing the risk of a systemic activation of the coagulation system.

FVIIa exists in plasma mainly as a single-chain zymogen, which is cleaved by FXa into its two-chain, activated form, FVIIa. Recombinant activated factor VIIa (rFVIIa) has been developed as a pro-haemostatic agent. The administration of rFVIIa offers a rapid and highly effective pro-haemostatic response in haemophilic subjects with bleedings who cannot be treated with coagulation factor products due to antibody formation. Also bleeding subjects with a factor VII deficiency can be treated successfully with FVIIa. In these studies, no unfavourable side effects of rFVIIa (in particular the occurrence of thromboembolism) has been encountered.

Extra exogenously administered FVIIa increases the formation of thrombin on the activated platelet surface. This occurs in haemophilia subjects lacking FIX or FVIII and therefore missing the most potent pathway for full thrombin formation. Also in the presence of a lowered number of platelets or platelets with a defect function, extra FVIIa increases the thrombin formation and is haemostatically effective in subjects.

The coagulation factors of the extrinsic pathway are inhibited by EPI (Extrinsic Pathway Inhibitor) now called TFPI (Tissue Factor Pathway Inhibitor). TFPI is a Kunitz type protease inhibitor which binds and inhibits FXa. The TFPI-FXa complex inhibits FVIIa-TF (Rapaport, Blood 73, p 359, 1989). The significance of TFPI for the coagulation reaction has not yet been established since only unphysiological high concentrations affects conventional coagulation assays (Broze et al., Bio-chemistry 29, p 7539, 1990). Therefore, TFPI activity is measured in sophisticated assays where TFPI is allowed to bind FXa and the TFPI-FXa is added to TF-FVII reactants that may activate FIX or FX (Bajaj et al., J Clin Invest 79, p 1974, 1987; Sandset et al., Thromb Res 47, p 389, 1987).

It is well known that subjects who bleed excessively in association with surgery or major trauma and need blood transfusions develop more complications than those who do not experience any bleeding. However, also moderate bleedings requiring the administration of human blood or blood products (platelets, leukocytes, plasma-derived concentrates for the treatment of coagulation defects, etc.) may lead to complications associated with the risk of transferring human viruses (hepatitis, HIV, parvovirus, and other, by now unknown viruses). Extensive bleedings requiring massive blood transfusions may lead to the development of multiple organ failure including impaired lung and kidney function. Once a subject has developed these serious complications a cascade of events involving a number of cytokines and inflammatory reactions is started making any treatment extremely difficult and unfortunately often unsuccessful. Therefore a major goal in surgery as well as in the treatment of major tissue damage is to avoid or minimise the bleeding To avoid or minimise such bleeding it is of importance to ensure the formation of stable and solid haemostatic plugs that are not easily dissolved by fibrinolytic enzymes. Furthermore, it is of importance to ensure quick formation of such plugs or clots.

European Patent No. 225.160 (Novo Nordisk) concerns compositions of FVIIa and methods for the treatment of bleeding disorders not caused by clotting factor defects or clotting factor inhibitors.

European Patent No. 82.182 (Baxter Travenol Lab.) concerns a composition of factor VIIa for use in counteracting deficiencies of blood clotting factors or the effects of inhibitors to blood clotting factors in a subject.

International Patent Publication No. WO 93/06855 (Novo Nordisk) concerns the topical application of FVIIa.

European Patent No. 558529 (Novo Nordisk) concerns compositions for the treatment of patients with prolonged coagulation time, the composition containing, as an active component, an EPI inhibitor.

International Patent Publication No. WO 96/28153 (Novo Nordisk) and U.S. Pat. No. 5,622,988 (Novo Nordisk) concerns novel compounds which show activity in inhibiting Tissue Factor Pathway Inhibitor (TFPI), and therefore can be used in reducing coagulation time in medical conditions which are characterized by excess or uncontrolled bleeding.

There remains a need in the art for an improved, reliable and widely applicable method of enhancing thrombin generation, forming quick stable haemostatic plugs and achieving full haemostasis in subjects, in particular in subjects having an impaired thrombin generation. There is also a need for a method wherein the amount of FVIIa needed for achieving full haemostasis is lowered.

BRIEF DESCRIPTION OF THE DRAWINGS

FIG. 2 is a graphic representation of the effect of anti-TFPI IgG on thrombin generation in a cell-based model system. Unactivated platelets were mixed with factors V, VIII, X, IX, VII, VIIa (0.1 nM), prothrombin, ATIII, TFPI, and calcium, and added to tissue factor-expressing monocytes. Aliquots were removed and analyzed for thrombin amidolytic activity. Thrombin generation at normal conditions (non-hemophilia) is shown with ●. Hemophilia A-like conditions (○) were mimicked by omitting factor VIII and preincubating the platelets with an anti-factor VIII IgG. Anti-TFPI IgG at 0.1 µg/ml (■, dotted line); 1 µg/ml (▲, solid line); 10 µg/ml (◆, dotted line); and 100 µg/ml (□, solid line) was added to hemophilia A-like conditions is shown in FIG. 2A. The effect on thrombin generation upon addition of 50 nM rFVIIa (▲, solid line); 10 µg/ml anti-TFPI IgG (◆, dotted line); and 50 nM rFVIIa combined with 10 µg/ml anti-TFPI IgG (□, solid line) at hemophilia A-like conditions is shown in FIG. 2B.

FIG. 3A: rFVIIa was added to hemophilia A-like conditions at final concentrations of 0.1 nM reflecting a physiologically relevant concentration of factor VIIa (○, solid line); or 50 nM (Δ, dotted line); 500 nM (▲, solid line); 1 µM (◆, dotted line); and 1.8 µM (□, solid line). FIG. 3B: hemophilia A-like conditions with rFVIIa at 0.1 nM (○, solid line); rFVIIa at 1 µM (▲, solid line); anti-TFPI IgG at 10 µg/ml (◆, dotted line); and the combination of 1 µM rFVIIa and 10 µg/ml anti-TFPI IgG (□, solid line) are shown.

SUMMARY OF THE INVENTION

The present invention provides pharmaceutical compositions comprising (i) Factor VIIa or a Factor VIIa variant and (ii) a TFPI inhibitor. In some embodiments, the Factor VIIA is human FVIIa. In some embodiments, the composition further comprises FVIII or a Factor VIII variant.

In another aspect, the invention provides kits containing a treatment for bleeding episodes that comprise:
a) an effective amount of a factor VIIa and a pharmaceutically acceptable carrier in a first unit dosage form;
b) an effective amount of a TFPI inhibitor and a pharmaceutically acceptable carrier in a second unit dosage form; and
c) a container means for containing the first and second dosage forms.

In some embodiments, the kits also contain Factor VIII or a Factor VIII variant.

In another aspect, the invention provides methods for treating a bleeding episode in a subject in need of such treatment, which are carried out by administering to said subject (i) a first amount of Factor VIIa or a Factor VIIa variant and (ii) a second amount of a TFPI inhibitor, wherein the first and second amounts together are effective for treating the bleeding episode.

In some embodiments, the Factor VIIa or Factor VIIa variant and the TFPI inhibitor are administered in a single dosage form. In other embodiments, the Factor VIIa or Factor VIIa variant and the TFPI inhibitor are administered sequentially.

In another aspect, the invention provides methods of enhancing coagulation in a subject, which are carried out by administering to said subject (i) a first amount of Factor VIIa or a Factor VIIa variant and (ii) a second amount of a TFPI inhibitor, wherein said first and second amounts together are effective for enhancing coagulation.

DETAILED DESCRIPTION OF THE INVENTION

One object of the present invention is to provide compositions, which can effectively be used in the treatment or prophylaxis of bleeding episodes and coagulation disorders.

A second object of the present invention is to provide compositions in one dosage form, which can effectively be used in the treatment or prophylaxis of bleeding episodes or as a procoagulant.

Another object of the present invention is to provide compositions, method of treatment or kits exhibiting a synergistic effect.

A further object of the present invention is to provide compositions, method of treatment or kits exhibiting no substantial side effects, such as a high level of systemic activation of the coagulation system.

Other objects of the present invention will become apparent upon reading the present description.

The present inventors have shown that a combination of a FVIIa and a TFPI inhibitor can reduce the clotting time of normal human plasma as well as of FVIII-deficient plasma more effectively than either FVIIa or TFPI inhibitor alone. By combining a FVIIa at a concentration where no further decrease in clotting time was observed with a TFPI inhibitor also at a concentration where no further decrease in clotting time was observed it was unexpectedly shown that a further reduction in clotting time was obtained. Thus, by enhancing coagulation a more effective treatment of bleeding in subjects can be obtained. Moreover, patients can be treated with relatively lower concentrations of FVIIa, thus, reducing the relatively high costs in connection with conventional treatment with FVIIa alone. It has also been shown that combination of a FVIIa and a TFPI inhibitor can increase thrombin generation in FVIII-deficient plasma more effectively than either FVIIa or TFPI inhibitor alone. It has also been shown that combination of a FVIIa and a TFPI inhibitor can prolong the in vitro clot lysis time in normal human plasma more effectively than either FVIIa or TFPI inhibitor alone In a first aspect, the invention relates to a pharmaceutical composition comprising a Factor VIIa and a TFPI inhibitor and, optionally, a pharmaceutically acceptable carrier.

In another aspect, the invention relates to a pharmaceutical composition comprising a Factor VIIa and a TFPI inhibitor as the sole active agents and, optionally, a pharmaceutically acceptable carrier.

In another aspect, the invention relates to a pharmaceutical composition formulated for intravenous administration comprising a Factor VIIa and a TFPI inhibitor and, optionally, a pharmaceutically acceptable carrier.

In another aspect, the invention relates to a pharmaceutical composition formulated for intravenous administration comprising a Factor VIIa and a TFPI inhibitor as the sole active agents and, optionally, a pharmaceutically acceptable carrier.

In another aspect, the invention relates to the use of a factor VIIa in combination with a TFPI inhibitor for the manufacture of a medicament for reducing clotting time of mammalian plasma.

In another aspect, the invention relates to the use of a factor VIIa in combination with a TFPI inhibitor for the manufacture of a medicament for reducing clotting time of mammalian plasma.

In another aspect, the invention relates to the use of a factor VIIa in combination with a TFPI inhibitor for the manufacture of a medicament for reducing clotting time of normal mammalian plasma.

In another aspect, the invention relates to the use of a factor VIIa in combination with a TFPI inhibitor for the manufacture of a medicament for reducing clotting time of factor VIII-deficient plasma.

In another aspect, the invention relates to the use of a factor VIIa in combination with a TFPI inhibitor for the manufacture of a medicament for prolonging the clot lysis time in mammalian plasma.

In another aspect, the invention relates to the use of a factor VIIa in combination with a TFPI inhibitor for the manufacture of a medicament for prolonging the clot lysis time in normal mammalian plasma.

In another aspect, the invention relates to the use of a factor VIIa in combination with a TFPI inhibitor for the manufacture of a medicament for increasing thrombin generation in factor VIII-deficient plasma.

In another aspect, the invention relates to the use of a factor VIIa in combination with a TFPI inhibitor for the manufacture of a medicament for enhancing coagulation of mammalian plasma.

In another aspect, the invention relates to the use of a factor VIIa in combination with a TFPI inhibitor for the manufacture of a medicament for treating bleeding episodes or for coagulative treatment.

In another aspect, the invention relates to the use of a factor VIIa in combination with a TFPI inhibitor as the sole active agents for the manufacture of a medicament for reducing clotting time of mammalian plasma.

In another aspect, the invention relates to the use of a factor VIIa in combination with a TFPI inhibitor as the sole active agents for the manufacture of a medicament for reducing clotting time of normal mammalian plasma.

In another aspect, the invention relates to the use of a factor VIIa in combination with a TFPI inhibitor as the sole active agents for the manufacture of a medicament for reducing clotting time of factor VIII-deficient plasma.

In another aspect, the invention relates to the use of a factor VIIa in combination with a TFPI inhibitor as the sole active agents for the manufacture of a medicament for enhancing coagulation of mammalian plasma.

In another aspect, the invention relates to the use of a factor VIIa in combination with a TFPI inhibitor as the sole active agents for the manufacture of a medicament for treating bleeding episodes or for coagulative treatment.

In another aspect, the invention relates to the use of a factor VIIa in combination with a TFPI inhibitor for the manufacture of a medicament for treating impaired thrombin generation in a subject, including a human being. In an embodiment the subject is a multitransfused subject, including a human being.

In another aspect, the invention relates to the use of a factor VIIa in combination with a TFPI inhibitor as the sole active agents for the manufacture of a medicament for treating impaired thrombin generation in a subject, including a human being. In an embodiment the subject is a multitransfused subject, including a human being.

In another aspect, the invention relates to a method of reducing clotting time of mammalian plasma, which method comprises administering to a mammal an effective amount of a factor VIIa in combination with an effective amount of a TFPI inhibitor.

In another aspect, the invention relates to a method of reducing clotting time of normal mammalian plasma, which method comprises administering to a mammal an effective amount of a factor VIIa in combination with an effective amount of a TFPI inhibitor.

In another aspect, the invention relates to a method of reducing clotting time of factor VIII-deficient mammalian plasma, which method comprises administering to a mammal an effective amount of a factor VIIa in combination with an effective amount of a TFPI inhibitor.

In another aspect, the invention relates to a method for prolonging the clot lysis time in normal mammalian plasma, which method comprises administering to a mammal an effective amount of a factor VIIa in combination with an effective amount of a TFPI inhibitor.

In another aspect, the invention relates to a method for prolonging the in vitro clot lysis time in normal mammalian plasma, which method comprises administering to a mammal an effective amount of a factor VIIa in combination with an effective amount of a TFPI inhibitor.

In another aspect, the invention relates to a method for increasing thrombin generation in factor VIII-deficient plasma, which method comprises administering to a mammal an effective amount of a factor VIIa in combination with an effective amount of a TFPI inhibitor.

In another aspect, the invention relates to a method of enhancing coagulation of mammalian plasma, which method comprises administering to a mammal an effective amount of a factor VIIa in combination with an effective amount of a TFPI inhibitor.

In another aspect, the invention relates to a method for treating bleeding episodes in a subject comprising administering to a subject an effective amount of a Factor VIIa in combination with an effective amount of a TFPI inhibitor.

In another aspect, the invention relates to a method of reducing clotting time of mammalian plasma, which method comprises administering to a mammal an effective amount of a factor VIIa in combination with an effective amount of a TFPI inhibitor as the sole active agents.

In another aspect, the invention relates to a method of reducing clotting time of normal mammalian plasma, which method comprises administering to a mammal an effective amount of a factor VIIa in combination with an effective amount of a TFPI inhibitor as the sole active agents.

In another aspect, the invention relates to a method of reducing clotting time of factor VIII-deficient mammalian plasma, which method comprises administering to a mammal an effective amount of a factor VIIa in combination with an effective amount of a TFPI inhibitor as the sole active agents.

In another aspect, the invention relates to a method of enhancing coagulation of mammalian plasma, which method comprises administering to a mammal an effective amount of a factor VIIa in combination with an effective amount of a TFPI inhibitor as the sole active agents.

In another aspect, the invention relates to a method for treating bleeding episodes in a subject comprising administering to a subject an effective amount of a Factor VIIa in combination with an effective amount of a TFPI inhibitor as the sole active agents.

In another aspect, the invention relates to a kit containing a treatment for bleeding episodes or for coagulative treatment comprising
a) an effective amount of a factor VIIa and a pharmaceutically acceptable carrier in a first unit dosage form;
b) an effective amount of a TFPI inhibitor and a pharmaceutically acceptable carrier in a second unit dosage form; and container means for containing said first and second dosage forms.

In another aspect, the invention relates to a kit containing a treatment for bleeding episodes or for coagulative treatment consisting essentially of
a) an effective amount of a factor VIIa and a pharmaceutically acceptable carrier in a first unit dosage form;
b) an effective amount of a TFPI inhibitor and a pharmaceutically acceptable carrier in a second unit dosage form; and container means for containing said first and second dosage forms.

In one embodiment, the factor VIIa is recombinant Factor VIIa.

In a further embodiment the factor VIIa is recombinant human Factor VIIa.

In a further embodiment the factor VIIa is a Factor VIIa variant.

In a further embodiment, the FVIIa variants are amino acid sequence variants having no more than 20 amino acids replaced, deleted or inserted compared to wild-type FVIIa (i.e., a polypeptide having the amino acid sequence disclosed in U.S. Pat. No. 4,784,950). In a further embodiment, the FVIIa variants have no more than 15 amino acids replaced, deleted or inserted; in a further embodiment, the FVIIa variants have no more than 10 amino acids replaced, deleted or inserted; in a further embodiment, the FVIIa variants have no more than 8 amino acids replaced, deleted or inserted; in a further embodiment, the FVIIa variants have no more than 6 amino acids replaced, deleted or inserted; in a further embodiment, the FVIIa variants have no more than 5 amino acids replaced, deleted or inserted compared to wild-type FVIIa. In a further embodiment, the FVIIa variants have no more than 3 amino acids replaced, deleted or inserted compared to wild-type FVIIa.

In a further embodiment the TFPI inhibitor is selected from TFPI inhibitors which can be identified like FVIII inhibiting antibodies in Bethesda assay as described in EP 0558529. In a further embodiment the TFPI inhibitor is selected from a polyclonal or monoclonal antibody, or a fragment thereof, a polypeptide, an oligopeptide, a short peptide, or a small organic molecule. Examples of small organic molecules (which are TFPI inhibitors) can be found in WO 96/28153 and U.S. Pat. No. 5,622,988.

In a further embodiment, mammalian plasma is human plasma.

In a further embodiment, the factor VIIa and the TFPI inhibitor are administered simultaneously and in one-dosage form. In another embodiment, the factor VIIa and the TFPI inhibitor is administered sequentially. In a further embodiment, the factor VIIa and the TFPI inhibitor is administered within 1–2 hours of each other, such as within 30 min of each other, for instance within 10 min of each other, e.g., in the form of a kit comprising factor VIIa in a first unit dosage form and TFPI inhibitor in a second unit dosage form.

In one embodiment, the effective amount of FVIIa is from 0.05 mg/day to 500 mg/day (70-kg subject).

In one embodiment of the present invention, the pharmaceutical composition (when in single-preparation form) consists essentially of a FVIIa, a TFPI inhibitor, and at least one pharmaceutical acceptable excipient or carrier, and optionally a stabiliser and/or a detergent and/or a neutral salt and/or an antioxidant and/or a preservative, and, optionally, a protease inhibitor.

In another embodiment, the pharmaceutical composition (when in form of a kit) consists of a first unit dosage form consisting essentially of a FVIIa and at least one pharmaceutical acceptable excipient or carrier, and optionally a stabiliser and/or a detergent and/or a neutral salt and/or an antioxidant and/or a preservative, and, optionally, a protease inhibitor; and a second unit dosage form consisting essentially of a TFPI inhibitor, and at least one pharmaceutical acceptable excipients or carrier, and optionally a stabiliser and/or a detergent and/or a neutral salt and/or an antioxidant and/or a preservative, and, optionally, a protease inhibitor.

In a further aspect, the composition further contains a factor VIII.

In one embodiment, the factor VIII is FVIIIa. In a further embodiment the factor VIII is recombinant Factor VIIIa. In a further embodiment the factor VIII is recombinant human Factor VIIIa.

In a further aspect, the composition further comprises an inhibitor of the fibrinolytic system, e.g., aprotinin, ε-aminocaproic acid or tranexamic acid.

In a further aspect, the invention relates to a kit containing a treatment for bleeding episodes or for coagulative treatment comprising
a) an effective amount of a factor VIIa and a pharmaceutically acceptable carrier in a first unit dosage form;
b) an effective amount of a TFPI inhibitor and a pharmaceutically acceptable carrier in a second unit dosage form;
c) an effective amount of a factor VIII or factor VIIIa and a pharmaceutically acceptable carrier in a third unit dosage form; and
d) container means for containing said first, second and third dosage forms.

In a further aspect, the invention relates to a kit containing a treatment for bleeding episodes or for coagulative treatment comprising
a) an effective amount of a factor VIIa and a TFPI inhibitor and a pharmaceutically acceptable carrier in a first unit dosage form;
b) an effective amount of a factor VIII or factor VIIIa and a pharmaceutically acceptable carrier in a second unit dosage form; and
c) container means for containing said first and second dosage forms.

In another aspect, the invention relates to a kit containing a treatment for bleeding episodes or for coagulative treatment comprising
a) an effective amount of a factor VIIa and a pharmaceutically acceptable carrier in a first unit dosage form;
b) an effective amount of a factor VIII or factor VIIIa and a TFPI inhibitor and a pharmaceutically acceptable carrier in a second unit dosage form; and
c) container means for containing said first and second dosage forms.

The present invention provides a composition comprising a combination of a factor VIIa and a TFPI inhibitor. The invention also provides a composition comprising a combination of a factor VIIa and a TFPI inhibitor as the sole active ingredients. The composition may be in the form of a single composition or it may be in the form of a multi-component kit. The present compositions are useful as therapeutic and prophylactic procoagulant and forms quick fibrin clots in mammals, including primates such as humans.

Whenever, a first or second unit dose is mentioned throughout this specification this does not indicate the preferred order of administration, but is merely done for convenience purposes.

The present invention further provides a method for treating (including prophylactically treating or preventing) bleeding episodes in a subject, including a human being, e.g., due to trauma or surgery, or in subjects lacking or having defective blood coagulation factors FIX or FVIII or platelets.

The present invention further provides a method for treating (including prophylactically treating or preventing) an impaired thrombin generation in a subject, including a human being. In an embodiment the subject is a multitransfused subject, including a human being.

It has now been found that a combination of a FVIIa and a TFPI inhibitor is an advantageous product ensuring the formation of fast haemostatic plugs.

In the presence of a TFPI inhibitor lower concentrations of FVIIa may be sufficient to ensure full haemostasis.

The full thrombin generation is necessary for a solid, stable haemostatic plug to be formed. The fibrin structure of such a plug is dependent on both the amount of thrombin formed and the rate of the initial thrombin generation. In the presence of an impaired thrombin generation a porous fibrin plug, which is highly permeable, is being formed. The fibrinolytic enzymes normally present on the fibrin surface easily dissolve such a fibrin plug. The formation of a stable fibrin plug is also dependent on the presence of FXIIIa, which is being activated by thrombin and therefore also dependent on the full thrombin generation. Furthermore, the recently described thrombin-activatable fibrinolytic inhibitor, TAFI, requires rather high thrombin amounts for its activation. In the presence of a not fully adequate thrombin formation the TAFI may therefore not be activated resulting in the formation of a haemostatic plug, which is easier than normally dissolved by the normal fibrinolytic activity.

Subjects with thrombocytopenia have an impaired thrombin generation as well as a defective stabilization of the fibrin plugs resulting in haemostatic plugs prone to premature dissolution. Furthermore, subjects subjected to major trauma or organ damage and who, as a consequence, have obtained frequent blood transfusions often have lowered platelet counts as well as lowered levels of fibrinogen, FVIII, and other coagulation proteins. These subjects experience an impaired (or lowered) thrombin generation. In addition, their lowered fibrinogen level interfere negatively with the activation of FXIII. These subjects, therefore, have a defective, or less efficient, haemostasis leading to the formation of fibrin plugs which are easily and prematurely dissolved by proteolytic enzymes, such enzymes in addition being extensively released in situations characterized by extensive trauma and organ damage.

In order to facilitate the formation of fully stabilized plugs with full capacity to maintain haemostasis in a subject, a composition according to the invention is administered. This composition is especially beneficial in subjects with a lowered number of platelets and in subjects with lowered plasma levels of fibrinogen and/or other coagulation proteins.

The factor VIIa used in the present invention may be purified from blood or produced by recombinant means. It is evident that the practice of the methods described herein is independent of how the purified Factor VIIa is derived and, therefore, the present invention is contemplated to cover use of any factor VIIa preparation suitable for use herein. Preferred is human FVIIa. Also genetically engineered variants of FVIIa retaining their characteristic haemostasis-related activity may be used in the present inventions. Fragments of factor VIIa, or FVIIa-variants retaining their characteristic haemostasis-related activity may also be used in the present inventions. The TFPI inhibitor used in the present invention may be identified like FVIII inhibiting antibodies in Bethesda assay as described in EP 0558529.

Non-limiting examples of Factor VII variants having substantially the same or better biological activity compared to wild-type Factor VIIa include, but are not limited to, those described in Danish Patent Applications Nos. PA 2000 00734, PA 2000 01360, PA 2000 01361, and PA 2001 00477. Non-limiting examples include [L305V]-FVIIa, [L305V/M306D/D309S]-FVIIa, [L305I]-FVIIa, [L305T]-FVIIa, [F374P]-FVIIa, [V158T/M298Q]-FVIIa, [V158D/E296V/M298Q]-FVIIa and [K337A]-FVIIa.

It will be apparent to those skilled in the art that substitutions can be made outside the regions critical to the function of the FVIIa or TFPI inhibitor-molecule and still result in an active polypeptide. Amino acid residues essential to the activity of the FVII-polypeptide (or optionally the TFPI inhibitor-polypeptide), and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The introduction of a mutation into the nucleic acid sequence to exchange one nucleotide for another nucleotide may be accomplished by site-directed mutagenesis using any of the methods known in the art. Particularly useful is the procedure that utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl, which is specific for methylated and hemimethylated DNA to digest the parental DNA template and to select for mutation-containing synthesized DNA. Other procedures known in the art for creating, identifying and isolating variants may also be used, such as, for example, gene shuffling or phage display techniques.

In the present context the three-letter or one-letter indications of the amino acids have been used in their conventional meaning as indicated in table 2. Unless indicated explicitly, the amino acids mentioned herein are L-amino acids. It is to be understood, that the first letter in, for example, K337 represent the amino acid naturally present at the indicated position of native (wild-type) human factor VIIa, and that, for example, [K337A]-FVIIa designates the FVII-variant wherein the amino acid represented by the one-letter code K naturally present in the indicated position in native (wild-type) human factor VIIa is replaced by the amino acid represented by the one-letter code A.

TABLE 2

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |

The term "factor VIIa", "Factor VIIa" or "FVIIa" may be used interchangeably. The term factor VIIa includes zymogen factor VII (single-chain factor VII).

The term "factor VIII" has its usual meaning (coagulation factor VIII) and includes activated factor VIII (designated FVIIIa) and truncated forms of factor VIII retaining its characteristic coagulant activity. The term "TFPI inhibitor" means compounds inhibiting the anti-coagulative activity of TFPI (tissue factor pathway inhibitor). The term includes compounds such as those defined in European Patent No. 558 529, and those described in WO 96/28153 and U.S. Pat. No. 5,622,988. A TFPI inhibitor (alternatively termed a TFPI antagonist) can be, without limitation, a polyclonal or monoclonal antibody or fragment(s) thereof, such as, for example F(ab')$_2$, or Fab fragments. The TFPI inhibitor can also be a linear or cyclic peptide inhibiting the activity of TFPI. The TFPI inhibitor can also be a small organic molecule, such as, for example, a molecule prepared by mimicking the spatial conformation of a peptide or identified by screening of any compound library or any other small organic molecule.

Within the present invention an "effective amount" of FVIIa and an "effective amount" of TFPI inhibitor is defined as the amount of FVIIa and TFPI inhibitor sufficient to prevent or reduce bleeding or blood loss, so as to cure, alleviate or partially arrest the disease and its complications.

The amount of FVIIa and the amount of TFPI inhibitor administered according to the present invention may, typically, vary from a ratio of about 1:100 to about 100:1 ($\mu$g FVIIa:$\mu$g TFPI inhibitor).

In this context, "subjects with an impaired thrombin generation" means subjects who cannot generate a full thrombin burst on the activated platelet surface and includes subjects having a generation of thrombin less that the thrombin-generation in subjects having a fully functioning, normal haemostatic system, including a normal amount and function of coagulation factors, platelets and fibrinogen, and includes subjects lacking FIX and/or FVIII (haemophilia A and B) or having defective FIX and/or FVIII or having inhibitors against FIX and/or FVIII; subjects lacking FXI; subjects with a lowered number of platelets or platelets with a defective function (e.g., thrombocytopenia or thrombasthenia Glanzmann or subjects with excessive bleeds); subjects having lowered levels of prothrombin, FX, or FVII; subjects with lowered plasma concentrations of fibrinogen (e.g., multitransfused subjects as a consequence of multiple trauma or extensive surgery).

The term "full haemostasis" means the formation of a stable and solid fibrin clot or plug at the site of injury which effectively stops the bleeding and which is not readily dissolved by the fibrinolytic system.

The term "activity of FVIIa" or "FVIIa-activity" means the ability to generate thrombin, the term also includes the ability to generate thrombin on the surface of activated platelets in the absence of tissue factor.

The term "enhancement of the normal haemostatic system" means an enhancement of the ability to generate thrombin.

As used herein the term "bleeding disorder" reflects any defect, congenital, acquired or induced, of cellular or molecular origin that is manifested in bleedings. Examples are clotting factor deficiencies (e.g. haemophilia A and B or deficiency of coagulation Factors XI or VII), clotting factor inhibitors, defective platelet function, thrombocytopenia or von Willebrand's disease.

The term "bleeding episodes" is meant to include uncontrolled and excessive bleeding which is a major problem both in connection with surgery and other forms of tissue damage. Uncontrolled and excessive bleeding may occur in subjects having a basically normal coagulation system (these subjects do however develop a coagulopathy as a result of the bleeding—dilution of coagulation proteins, increased fibrinolysis and lowered platelets due to a dilution effect of the bleeding) and subjects having coagulation or bleeding disorders. Clotting factor deficiencies (haemophilia A and B, deficiency of coagulation factors XI or VII) or clotting factor inhibitors may be the cause of bleeding disorders. Excessive bleedings also occur in subjects with a normally functioning blood clotting cascade (no clotting factor deficiencies or -inhibitors against any of the coagulation factors) and may be caused by a defective platelet function, thrombocytopenia or von Willebrand's disease. In such cases, the bleedings may be likened to those bleedings caused by haemophilia because the haemostatic system, as in haemophilia, lacks or has abnormal essential clotting "compounds" (such as platelets or von Willebrand factor protein) that causes major bleedings. In subjects who experience extensive tissue damage in association with surgery or vast trauma, the normal haemostatic mechanism may be overwhelmed by the demand of immediate haemostasis and they may develop bleeding in spite of a basically (pre-trauma) normal haemostatic mechanism. Achieving satisfactory haemostasis also is a problem when bleedings occur in organs such as the brain, inner ear region and eyes with limited possibility for surgical haemostasis. The same problem may arise in the process of taking biopsies from various organs (liver, lung, tumour tissue, gastrointestinal tract) as well as in laparoscopic surgery. Common for all these situations is the difficulty to provide haemostasis by surgical techniques (sutures, clips, etc.) which also is the case when bleeding is diffuse (haemorrhagic gastritis and profuse uterine bleeding). Acute and profuse bleedings may also occur in subjects on anticoagulant therapy in whom a defective haemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical haemostasis, and which may result in diffuse bleeding from a large area. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with haemophilia. In another embodiment, the bleeding is associated with haemophilia with aquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with haemorrhagic gastritis. In another embodiment, the bleeding is profuse uterine bleeding. In another embodiment, the bleeding is occurring in organs with a limited possibility for mechanical haemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The composition according to the invention may further comprise a factor VIII. Such a composition should preferably be administered to subjects who do not have inhibitors to FVIII.

Any possible combination of two or more of the embodiments described herein, is intended to be comprised within the scope of the present invention.

In this context, the term "treatment" is meant to include both prevention of an expected bleeding, such as, for example, in surgery, and regulation of an already occurring bleeding, such as, for example, in haemophilia or in trauma, with the purpose of inhibiting or minimising the bleeding. Prophylactic administration of FVIIa and TFPI inhibitor is thus included in the term "treatment".

The term "subject" as used herein is intended to mean any animal, in particular mammals, such as humans, and may, where appropriate, be used interchangeably with the term "patient".

| Abbreviations | |
|---|---|
| TF | tissue factor |
| FVII | factor VII in its single-chain, unactivated form |
| FVIIa | factor VII in its activated form |
| rFVIIa | recombinant factor VII in its activated form |
| FVIII | factor VIII in its zymogenic, unactivated form |

| Abbreviations | |
|---|---|
| rFVIII | recombinant FVIII |
| FVIIIa | factor VIII in its activated form |
| rFVIIIa | recombinant FVIIIa |
| TFPI | tissue factor pathway inhibitor |

Preparation of Compounds

Human purified factor VIIa suitable for use in the present invention is preferably made by DNA recombinant technology, e.g. as described by Hagen et al., *Proc. Natl. Acad. Sci. USA* 83: 2412–2416, 1986 or as described in European Patent No. 200.421 (ZymoGenetics, Inc.). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J. Biol. Chem.* 255 (4): 1242–1247, 1980 and Hedner and Kisiel, *J. Clin. Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX a or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like.

As will be appreciated by those skilled in the art, it is preferred to use a TFPI inhibitor and a factor VIIa syngeneic with the subject in order to reduce the risk of inducing an immune response. The present invention also encompasses the use of such TFPI inhibitor and factor VIIa within veterinary procedures.

Administration and Pharmaceutical Compositions

For treatment in connection with deliberate interventions, the Factor VIIa and TFPI inhibitor will typically be administered within about 24 hours prior to performing the intervention, and for as much as 7 days or more thereafter. Administration as a coagulant can be by a variety of routes as described herein.

The typical dose of the Factor VIIa ranges from about 0.05 mg to about 500 mg/day, preferably from about 1 mg to about 200 mg/day, and more preferably from about 10 mg to about 175 mg/day for a 70-kg subject as loading and maintenance doses, depending on the weight of the subject and the severity of the condition.

With respect to the TFPI inhibitor, the dose should be sufficient to neutralize at least part of the TFPI activity in the patient treated. If the inhibitor is an antibody, the effective plasma concentration includes, without limitation, about 1–100 $\mu$g/ml (corresponding to about 40 $\mu$g/kg–4 mg/kg administrated i.v.) Alternatively, the plasma concentration includes be 0.1 $\mu$g–1 mg/ml (corresponding to administered doses of approximately 4 $\mu$g/kg–40 mg/kg). If the inhibitor is a peptide or a small organic molecule, the dose should be sufficient to ensure a plasma concentration of between about 0.3 ng/ml–1 mg/ml, preferably, about 3 ng/ml–100 µg/ml.

The compositions and kits of the present invention are useful within human and veterinary medicine, such as, for example, in the treatment or prophylaxis of subjects suffering from bleeding episodes or coagulative disorders. For use within the present invention, the factor VIIa and TFPI inhibitor are formulated, optionally with a pharmaceutically acceptable carrier. Preferably, the pharmaceutical compositions are administered parenterally, i.e., intravenously, subcutaneously, or intramuscularly, or it may be administered by continuous or pulsatile infusion. Alternatively, the TFPI inhibitor may be administered orally, in case a small organic molecule is considered, such as those disclosed in WO 96/28153 and U.S. Pat. No. 5,622,988.

Formulations may further include one or more diluents, emulsifiers, preservatives, buffers, excipients, etc. and may be provided in such forms as liquids, powders, emulsions, controlled release, etc. One skilled in this art may formulate the compositions of the invention an appropriate manner, and in accordance with accepted practices, such as those disclosed in *Remington's Pharmaceutical Sciences*, Gennaro, ed., Mack Publishing Co., Easton, Pa., 1990. The compositions for parenteral administration comprise the Factor VII and TFPI inhibitor in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII variants of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282.

A typical pharmaceutical composition for intravenous infusion could be made up to contain 250 ml of sterile Ringer's solution and 10 mg of the Factor VII variant. Actual methods for preparing parenterally administrable compositions will be known or apparent to those skilled in the art and are described in more detail in, for example, *Remington's Pharmaceutical Sciences*, 18th ed., Mack Publishing Company, Easton, Pa. (1990).

In short, pharmaceutical compositions suitable for use according to the present invention is made by mixing the FVIIa, or the TFPI inhibitor, or the FVIIa in combination with the TFPI inhibitor, preferably in purified form, with suitable adjuvants and a suitable carrier or diluent. Suitable physiological acceptable carriers or diluents include sterile water and saline. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Suitable adjuvants also include calcium, proteins (e.g. albumins), or other inert peptides (e.g. glycylglycine) or amino acids (e.g. glycine, or histidine) to stabilise the purified factor VIIa and/or TFPI inhibitor. Other physiological acceptable adjuvants are non-reducing sugars, polyalcohols (e.g. sorbitol, mannitol or glycerol), polysaccharides such as low molecular weight dextrins, detergents (e.g. polysorbate) and antioxidants (e.g. bisulfite and ascorbate). The adjuvants are generally present in a concentration of from 0.001 to 4% w/v. The pharmaceutical composition may also contain protease inhibitors, e.g. aprotinin or tranexamic acid, and preserving agents. Furthermore, the preparation may also contain a factor VIII.

The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The concentration of Factor VIIa, TFPI inhibitor or FVIIa in combination with TFPI inhibitor in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Administration by injection or infusion, in particular injection, is preferred. Thus, the factor VIIa and TFPI inhibitor are prepared in a form suitable for intravenous administration, such as a preparation that is either a dissolved lyophilised powder or a liquid formulation containing both the factor VIIa and the TFPI inhibitor in one dosage form, or a dissolved lyophilised powder or a liquid formulation containing the factor VIIa in one dosage form and dissolved lyophilised powder or a liquid formulation containing the TFPI inhibitor in another dosage form.

Local delivery of the Factor VIIa and TFPI inhibitor, such as, for example, topical application may be carried out, for example, by means of a spray, perfusion, double balloon catheters, stent, incorporated into vascular grafts or stents, hydrogels used to coat balloon catheters, or other well established methods. For ambulatory subjects requiring daily maintenance levels, the Factor VIIa and TFPI inhibitor may be administered by continuous infusion using e.g. a portable pump system. In any event, the pharmaceutical compositions should provide a quantity of Factor VIIa and TFPI inhibitor sufficient to effectively treat the subject.

The combination of a factor VIIa and a TFPI inhibitor shows a synergistic effect in an in vitro dilute prothrombin time-clotting assay. Moreover, the combination of a factor VIIa and a TFPI inhibitor shows a synergistic effect in enhancing coagulation.

The compositions containing the Factor VIIa and TFPI inhibitor can be administered for prophylactic and/or therapeutic treatments. In therapeutic applications, compositions are administered to a subject already suffering from a disease, as described above, in an amount sufficient to prevent or reduce bleeding or blood loss, so as to cure, alleviate or partially arrest the disease and its complications. An amount adequate to accomplish this is defined as an "effective amount" or "therapeutically effective amount". As will be understood by the person skilled in the art amounts effective for this purpose will depend on the severity of the disease or injury as well as the weight and general state of the subject.

It must be kept in mind that the materials of the present invention may generally be employed in serious disease or injury states, that is, life threatening or potentially life threatening situations. In such cases, in view of the minimisation of extraneous substances and general lack of immunogenicity of human Factor VII variants in humans, it is possible and may be felt desirable by the treating physician to administer a substantial excess of these variant Factor VII compositions.

In prophylactic applications, compositions containing the Factor VIIa and TFPI inhibitor are administered to a subject susceptible to or otherwise at risk of a disease state or injury to enhance the subject's own coagulative capability. Such an amount is defined to be a "prophylactically effective dose."

Single or multiple administrations of the compositions can be carried out with dose levels and patterns being selected by the treating physician. The compositions may be administered one or more times per day or week. An effective amount of such a pharmaceutical composition is the amount that provides a clinically significant effect against bleeding episodes. Such amounts will depend, in part, on the particular condition to be treated, age, weight, and general health of the subject, and other factors evident to those skilled in the art.

The composition is generally administered in one single dose, before the expected bleeding or at the start of the bleeding. It may however also be given in multiple doses, preferably with intervals of 2-4-6-12 hour, depending on the dose given and the condition of the subject.

The composition may be in the form of a single preparation comprising both FVIIa and TFPI inhibitor in suitable concentrations. The composition may also be in the form of a kit consisting of a first unit dosage form comprising FVIIa and a second unit dosage form comprising TFPI inhibitor and optionally one or more further unit dosage forms comprising a factor VIII. In this case, the FVIIa and the TFPI inhibitor should be administered sequentially, preferably within 1–2 hours of each other, such as within 30 min of each other, or preferably within 10 minutes or, more preferred, within 5 minutes of each other. Either of the two unit dosage forms can be administered first.

Since the present invention relates to the prevention or treatment of bleeding episodes or for coagulative treatment by treatment with a combination of active ingredients that may be administered separately, the invention also relates to combining separate pharmaceutical compositions in kit form. The kit includes at least two separate pharmaceutical compositions. The kit includes container means for containing the separate compositions such as a divided bottle or a divided foil packet. Typically the kit includes directions for the administration of the separate components. The kit form is particularly advantageous when the separate components are preferably administered in different dosage forms, are administered at different dosage intervals, or when titration of the individual components of the combination is desired by the prescribing physician.

Assays

Test for FVIIa Activity:

A suitable assay for testing for FVIIa activity and thereby selecting suitable Factor VIIa variants can be performed as a simple preliminary in vitro test:

In Vitro Hydrolysis Assay

Native (wild-type) Factor VIIa and Factor VIIa variant (both hereafter referred to as "Factor VIIa") may be assayed for specific activities. They may also be assayed in parallel to directly compare their specific activities. The assay is carried out in a microtiter plate (Max-iSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\ nm}$ Factor VIIa variant)/($A_{405\ nm}$ Factor VIIa wild-type).

Based thereon, Factor VIIa variants with an activity comparable to or higher than native Factor VIIa may be identified, such as, for example, variants where the ratio between the activity of the variant and the activity of native Factor VII is around, versus above 1.0.

The activity of Factor VIIa or Factor VIIa variants may also be measured using a physiological substrate such as factor X, suitably at a concentration of 100–1000 nM, where the factor Xa generated is measured after the addition of a suitable chromogenic substrate (eg. S-2765). In addition, the activity assay may be run at physiological temperature.

The ability of Factor VIIa or FVIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542–547 which is hereby incorporated as reference).

The present invention is further illustrated by the following examples, which, however, are not to be construed as limiting the scope of protection. The features disclosed in the foregoing description and in the following examples may, both separately and in any combination thereof, be material for realizing the invention in diverse forms thereof.

EXAMPLES

Anti-TFPI IgG may be obtained following the process described in the experimental part of EP 558529, which is incorporated herein by reference.

Example 1

The data presented here shows that the combination of rFVIIa at a concentration giving maximal shortening of the clotting time and anti-TFPI IgG at a concentration giving maximal shortening of the clotting time shortens the clotting time of normal human plasma as well as of factor VIII-deficient plasma more than rFVIIa and anti-TFPI IgG alone.

Methods

Clotting Assay

The clotting times were measured in a dilute PT-clotting assay. A volume of 180 μl factor VIII-deficient plasma (Helena Laboratories) or normal human plasma pool was mixed with 20 μl sample containing rFVIIa, anti TFPI-IgG or buffer (50 mM imidazole, 0.1 M NaCl, 1 mg/ml BSA, pH 7.4) and incubated 15 min at ambient temperature. The clotting times was then measured on an ACL 300R clotting instrument, where 75 μl of the samples were mixed with 75 μl thromboplastin/$CaCl_2$ reagent containing a 1:1200 dilution of Innovin (Dade) and 8.33 mM $CaCl_2$ in the imidazole buffer.

Results

Figure 1:
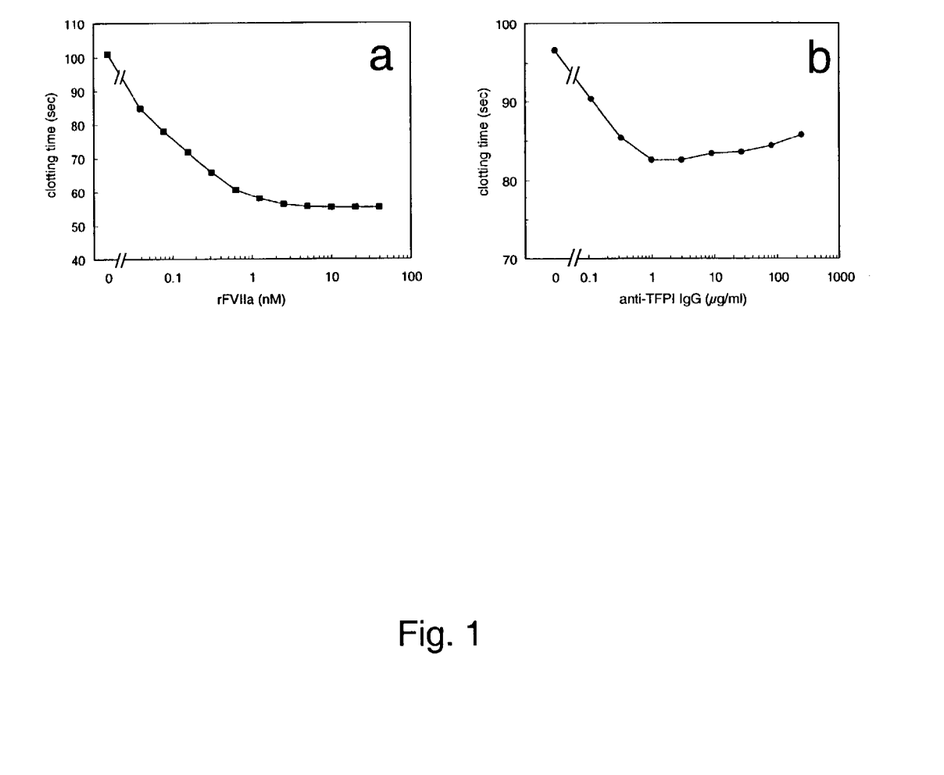
FIG. 1 is a graphic representation of the clotting times of normal human plasma after addition of the indicated concentrations of (a) rFVIIa or (b) anti-TFPI IgG. The concentrations noted are final concentrations after mixing with thromboplastin/CaCl$_2$ reagent.

The clotting times of normal human plasma preincubated with dilutions of rFVIIa and anti TFPI-IgG were determined (cf. FIG. 1).

Both rFVIIa and anti TFPI-IgG shortened the clotting time of normal human plasma in a dilute PT assay. rFVIIa at 0.04–1 nM gave a dose-dependent decrease in the clotting time. At rFVIIa concentrations above 5 nM no further decrease of the clotting time was observed. Anti-TFPI IgG at concentrations of 0.1–1 μg/ml shortened the clotting time in a dose-dependent manner. The shortening of the clotting time was less than observed for rFVIIa. At anti-TFPI IgG concentrations above 2 μg/ml no further shortening of the clotting time was observed.

rFVIIa and anti-TFPI IgG at concentrations giving maximal shortening of the clotting time (5 nM and 2.4 µg/ml, respectively) and concentrations giving partial shortening of the clotting time (0.5 nM and 0.1 µg/ml, respectively) were added to normal human plasma or factor VIII-deficient plasma and the clotting times determined (Table 1). By combining rFVIIa and anti-TFPI IgG the clotting time was shortened more than when rFVIIa or anti-TFPI IgG was added individually. This shows that a combination of rFVIIa and anti-TFPI IgG can be used for enhancing coagulation of hemophilia patients as well as for normal individuals.

Table 1. The effect of rFVIIa and anti-TFPI IgG alone or in combination on the clotting time of normal human plasma and factor VIII-deficient plasma. The values are mean of two samples.

|  | Clotting time (sec) | |
| --- | --- | --- |
|  | Normal human plasma | Factor VIII-deficient plasma |
| Buffer control | 93.8 | 108.6 |
| rFVIIa at 0.5 nM | 63.2 | 69.3 |
| rFVIIa at 5 nM | 57.2 | 61.6 |
| anti-TFPI IgG at 0.1 µg/ml | 85.4 | 103.8 |
| anti-TFPI IgG at 2.4 µg/ml | 83.4 | 97.2 |
| rFVIIa (0.5 nM) + anti-TFPI IgG (0.1 µg/ml) | 61.8 | 67.2 |
| rFVIIa (5 nM) + anti-TFPI IgG (2.4 µg/ml) | 52.6 | 57.0 |

Example 2

Methods.

The assay was performed essentially as described in Kjalke, M., Oliver, J. A., Monroe, D. M., Hoffman, M., Ezban, M., Hedner, U. & Roberts, H. R. (1997) The effect of active site-inhibited factor VIIa on tissue factor-initiated coagulation using platelets before and after aspirin administration. *Thrombosis and Haemostasis*, 78, 1202–1208. (Hereinafter Kjalke et al. 1997). Mononuclear cells were isolated from citrate-stabilized peripheral blood by density centrifugation, and % of monocytes determined by flow cytometry after labeling with a pycoerythrin-conjugated anti CD14 antibody (BD Pharmingen). The cells were resuspended in macro-phage serum-free media (Life Technologies) with 0.5 µg/ml LPS (Sigma L2755) and plated in 96-well tissue culture plates at a density of 20,000 monocytes/well. After one hour incubation at 37° C. in 5% $CO_2$, non-adherent cells, mainly lymphocytes, were removed by washing, and the incubation continued over night. The following day were unactivated platelets isolated from peripheral blood containing 5 µg/ml prostaglandin $E_1$ (Sigma) by density centrifugation and gel filtration on a Sepharose CL2B-column equilibrated with calcium-free tyrodes buffer (15 mM Hepes, 3.3 mM $Na_2PO_4$, pH 7.4, 138 mM NaCl, 2.7 mM KCl, 1 mM $MgCl_2$, 5.5 mM dextrose) containing 1 mg/ml BSA. The platelets were counted by flow cytometry using Tru-Count tubes (BD), and the platelet density adjusted with tyrodes buffer. rFVIIa (final concentration 0.1 nM or 50 nM, cf Thim, L., Bjoern, S., Christensen, M., Nicolaisen, E. M., Lund-Hansen, T., Pedersen, A. H. & Hedner, U. (1988) Amino acid sequence and posttranslational modifications of human factor VIIa from plasma and transfected baby hamster kidney cells. *Biochemistry*, 27, 7785–7793. (hereinafter Thim et al (1988)) were mixed with factor X (8 µg/ml, Haematologic Technologies Inc.), factor IX (5 µg/ml, Mononone, Armour Pharmaceutical), factor XI (5 µg/ml, Haematologic Technologies Inc.), prothrombin (86 µg/ml, Haematologic Technologies Inc), TFPI (0.1 µg/ml, cf Pedersen, A. H., Nordfang, O., Norris, F., Wiberg, F. C., Christensen, P. M., Moeller, K. B., Meidahl-Pedersen, J., Beck, T. C., Norris, K., Hedner, U. & Kisiel, W. (1990) Recombinant human extrinsic pathway inhibitor. Production, isolation, and characterization of its inhibitory activity on tissue factor-initiated coagulation reactions. *Journal of Biological Chemistry*, 265, 16786–16793. (Hereinafter Pedersen et al. (1990)), ATIII (120 µg/ml, Haematologic Technologies Inc), factor V (7 µg/ml, Haematologic Technologies Inc), factor VIII (1 U/ml, MeIATE, New York blood center), and calcium chloride (3 mM). Some of the proteins were pretreated as described (Kjalke et al. (1997). Proteins and platelets were added to the monocytes, and thrombin activity was measured by transferring aliquots to 9 volumes of HBS containing 1 mg/ml BSA, 1 mM EDTA, 50 µM Pefabloc Xa (Pentapharm), and 0.5 mM Chromozyme TH (Boehringer Mannheim). The color development was stopped with 2 M acetic acid, and A405 was measured. Human α-thrombin (Boehringer Mannheim) was used as standard.

Results.

Figure 2:
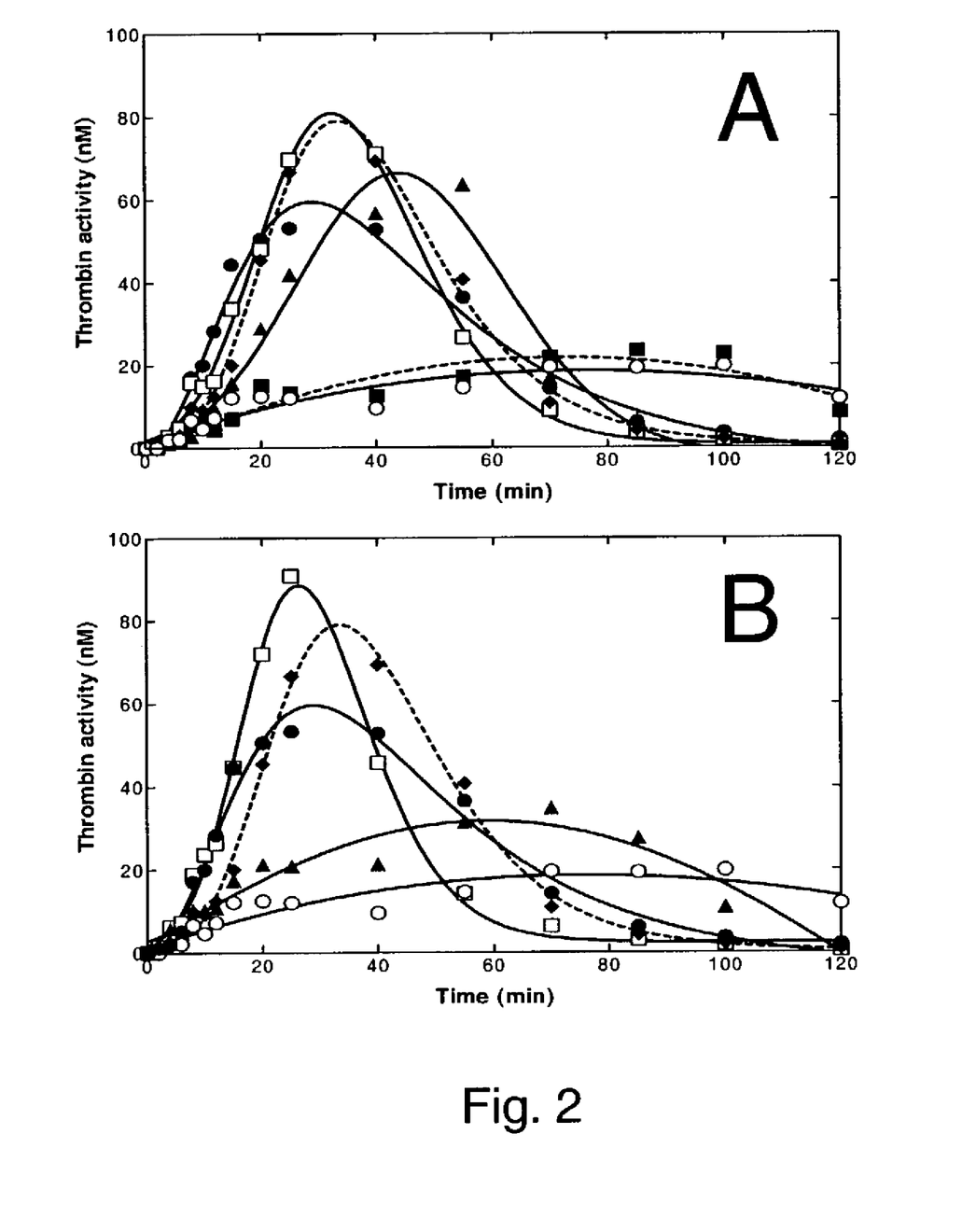
Figure 3:
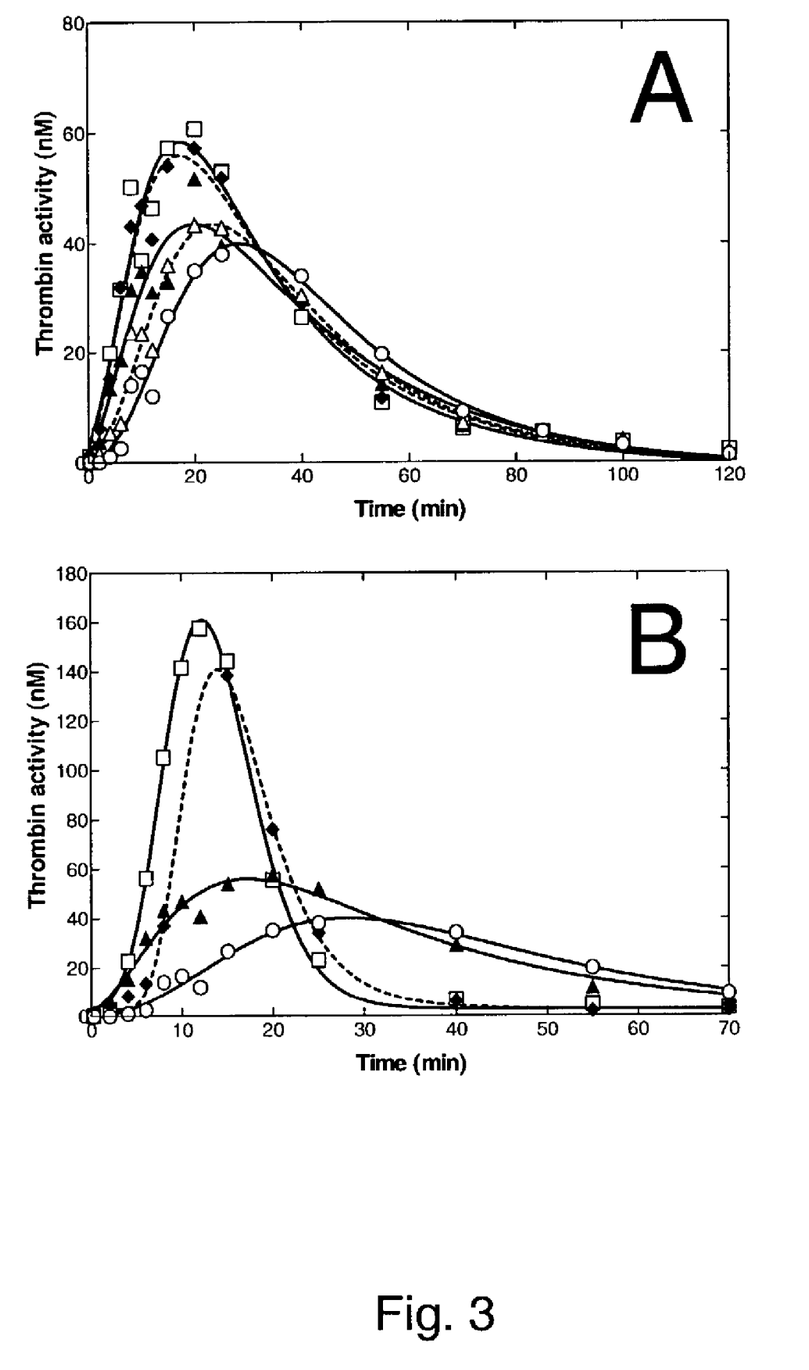
FIG. 3 is a graphic representation of the effect of rFVIIa on thrombin generation in a cell-based model system. The experimental details are as described for FIG. 2.

Hemophilia is characterized by impaired thrombin generation. This is illustrated in a cell-based model of tissue factor-initiated coagulation (Monroe, D. M., Roberts, H. R. & Hoffman, M. (1994) Platelet procoagulant complex assembly in a tissue factor-initiated system. *British Journal of Haematology*, 88, 364–371; (Hereinafter Monroe et al. 1994)); (Kjalke et al. 1997), where the maximal rate of thrombin generation was lowered, the time to maximal thrombin activity was delayed, and the peak level of thrombin activity was lowered at hemophilia A-like conditions compared to normal conditions (FIG. 2). When anti-TFPI IgG was added to hemophilia A-like conditions, a dose-dependent increase of the rate of thrombin generation, a shortening in the time to maximal thrombin activity, and an increase in the peak level of thrombin activity was observed (FIG. 2A). At concentrations above 10 µg/ml anti-TFPI IgG no further effect on thrombin generation was observed. rFVIIa at 50 nM also increased the thrombin generation at hemophilia A-like conditions as shown in FIG. 2B. Surprisingly, combining 50 nM rFVIIa with 10 µg/ml anti-TFPI IgG gave an earlier thrombin generation peak than it was possible to obtain with anti-TFPI IgG alone. When rFVIIa was added at increasing doses to hemophilia A-like conditions, a maximal effect, i.e. a maximal increase in ing doses to hemophilia A-like conditions, a maximal effect, i.e. a maximal increase in the maximal rate of thrombin generation, a maximal shortening in the time to maximal thrombin activity and a maximal increase in the peak level of thrombin activity was seen at 1 µM rFVIIa (FIG. 3A). Addition of higher concentrations of rFVIIa did not have any further effect on the thrombin generation curve. Addition of 10 µg/ml anti-TFPI IgG to the sample with 1 µM rFVIIa surprisingly increased the thrombin generation more than it was possible with rFVIIa alone as seen by an increased maximal rate of thrombin generation, a shortening in the time to maximal thrombin activity, and an increased maximal level of thrombin activity (FIG. 3B). Our data show, that combining rFVIIa and anti-TFPI IgG have an additional effect than simply increasing the concentration of one of the components alone.

Example 3

Methods.

Normal human plasma diluted 10-fold with buffer (20 mM HEPES, 150 mM NaCl, 5 mM CaCl, pH 7.4) containing Innovin (Dade Behring, 2000-fold dilution), rFVIIa (as indicated) and t-PA (tissue-type plasminogen activator, 8 nM; American Diagnostica) was added to 96-well ELISA plates and turbidity at 650 nm was measured at room temperature. Where indicated, a sheep anti-TFPI IgG (Enzyme Research Laboratories) was additionally included.

Results.

Figure 4:
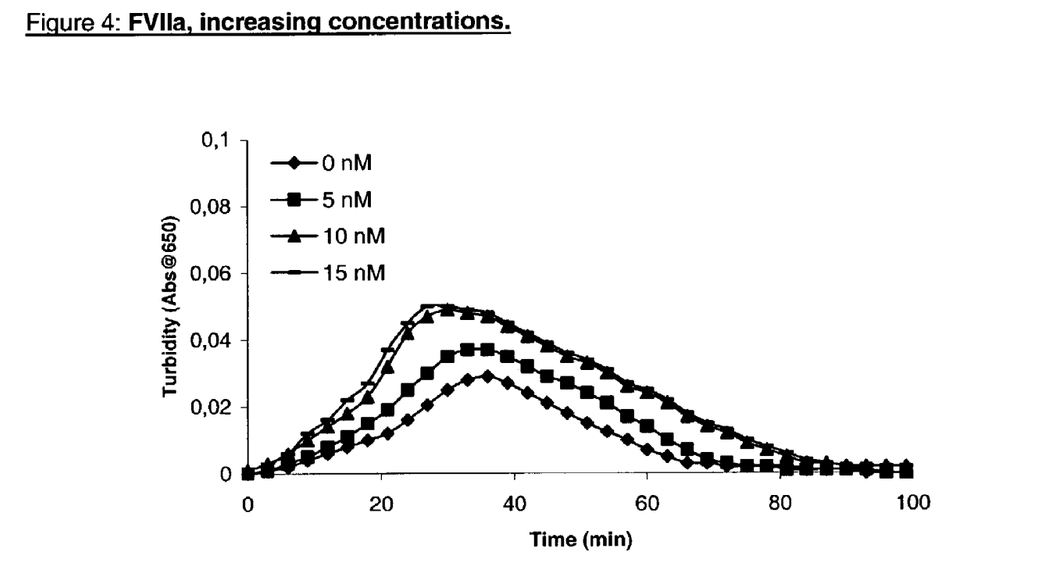
FIG. 4 is a graphic representation of the effect of increasing concentrations of Factor VIIa on clot lysis time.
Figure 5:
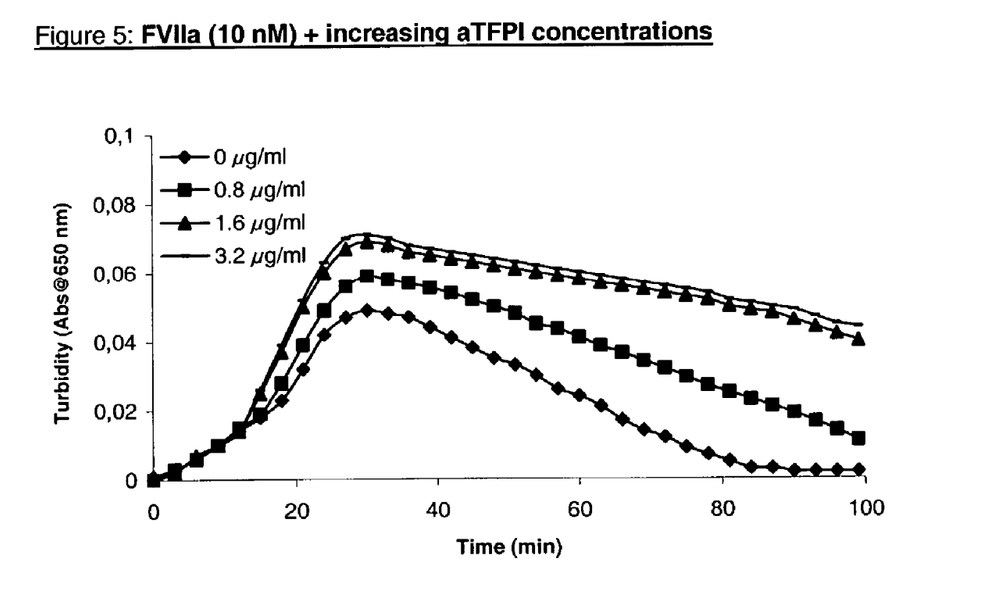
FIG. 5 is a graphic representation of the effect of increasing concentrations of Factor VIIa and aTFPI on clot lysis time.

FIG. 4 demonstrates that addition of rFVIIa results in a dose-dependent prolongation of the clot lysis time. This effect was optimal at 10 nM FVIIa; no additional effect was obtained by addition of 15 nM rFVIIa. However, addition of a sheep anti-TFPI IgG (aTFPI) resulted in a significant ($p<0.005$) further prolongation of the clot lysis time (see FIG. 5). The effect was dose-dependent and optimal at 1.6 $\mu$g/ml aTFPI. Taken together, these data show that combining rFVIIa and anti-TFPI IgG have an effect on the in vitro clot lysis which can not be obtained by simply increasing the concentration of one of the components alone.

The invention claimed is:

1. A pharmaceutical composition comprising (i) Factor VIIa or a Factor VIIa variant and (ii) a TFPI inhibitor.

2. The composition according to claim 1, wherein the Factor VIIa is human FVIIa.

3. The composition according to claim 1, wherein the Factor VIIa is recombinant FVIIa.

4. The composition according to claim 1, further comprising FVIII or a Factor VIII variant.

5. A kit containing a treatment for bleeding episodes comprising
   b) an effective amount of a factor VIIa and a pharmaceutically acceptable carrier in a first unit dosage form;
   b) an effective amount of a TFPI inhibitor and a pharmaceutically acceptable carrier in a second unit dosage form; and
   c) a container means for containing said first and second dosage forms.

6. A kit containing a treatment for bleeding episodes comprising
   a) an effective amount of a factor VIIa and a pharmaceutically acceptable carrier in a first unit dosage form;
   c) an effective amount of a TFPI inhibitor and a pharmaceutically acceptable carrier in a second unit dosage form;
   d) an effective amount of a factor VIII and a pharmaceutically acceptable carrier in a third unit dosage form; and
   e) a container means for containing said first, second, and third dosage forms.

7. A method for treating a bleeding episode in a subject in need of such treatment, said method comprising administering to said subject (i) a first amount of Factor VIIa or a Factor VIIa variant and (ii) a second amount of a TFPI inhibitor, wherein said first and second amounts together are effective for treating said bleeding episode.

8. A method according to claim 7, wherein the Factor VIIa or Factor VIIa variant and the TFPI inhibitor are administered in a single dosage form.

9. A method according to claim 7, wherein the Factor VIIa or Factor VIIa variant and the TFPI inhibitor are administered sequentially.

10. A method according to claim 7, wherein said treatment comprises reducing clotting time in said subject.

11. A method according to claim 7, wherein said treatment comprises prolonging clot lysis time in said subject.

12. A method according to claim 7, wherein said treatment comprises increasing thrombin generation in factor VIII-deficient plasma.

13. A method of enhancing coagulation in a subject, said method comprising administering to said subject (i) a first amount of Factor VIIa or a Factor VIIa variant and (ii) a second amount of a TFPI inhibitor, wherein said first and second amounts together are effective for enhancing coagulation.

* * * * *

UNITED STATES PATENT AND TRADEMARK OFFICE
CERTIFICATE OF CORRECTION

PATENT NO. : 7,015,194 B2
APPLICATION NO. : 10/271926
DATED : March 21, 2006
INVENTOR(S) : Kjalke It is certified that error appears in the above-identified patent and that said Letters Patent is hereby corrected as shown below:

Column 21, line 36, claim 5:
delete "b)" and insert --a)--.
Column 22, line 6, claim 6:
delete "c)" and insert --b)--.
Column 22, line 9, claim 6:
delete "d)" and insert --c)--.
Column 22, line 12, claim 6:
delete "e)" and insert --d)--.

Signed and Sealed this

Twentieth Day of November, 2007

JON W. DUDAS
*Director of the United States Patent and Trademark Office*